United States Patent
Hermansson et al.

(10) Patent No.: US 7,682,445 B2
(45) Date of Patent: Mar. 23, 2010

(54) POWDERED CBC SYSTEM WITH IMPROVED REACTION FEATURE

(75) Inventors: Leif Hermansson, Mölle (SE); Håkan Engqvist, Knivsta (SE)

(73) Assignee: DOXA AB, Uppsala (SE)

( * ) Notice: Subject to any disclaimer, the term of this patent is extended or adjusted under 35 U.S.C. 154(b) by 483 days.

(21) Appl. No.: 11/567,849

(22) Filed: Dec. 7, 2006

(65) Prior Publication Data

US 2007/0151485 A1    Jul. 5, 2007

Related U.S. Application Data

(60) Provisional application No. 60/748,176, filed on Dec. 8, 2005.

(51) Int. Cl.
| | |
|---|---|
| C04B 7/00 | (2006.01) |
| C04B 7/34 | (2006.01) |
| C04B 24/34 | (2006.01) |
| C04B 12/02 | (2006.01) |
| C04B 28/34 | (2006.01) |
| C04B 7/32 | (2006.01) |
| C04B 7/36 | (2006.01) |
| C09K 3/00 | (2006.01) |
| A01N 59/06 | (2006.01) |
| A61F 2/28 | (2006.01) |

(52) U.S. Cl. .................. 106/638; 106/658; 106/680; 106/690; 106/692; 106/35; 424/682; 623/23.62

(58) Field of Classification Search ................ 106/683, 106/680, 692, 695, 658, 728, 690, 691, 672, 106/674, 35, 713, 638; 424/682, 688; 433/226; 623/23.62

See application file for complete search history.

(56) References Cited

U.S. PATENT DOCUMENTS

| | | | | |
|---|---|---|---|---|
| 3,650,784 | A | * 3/1972 | Albert et al. | 106/672 |
| 4,084,981 | A | * 4/1978 | Higuchi et al. | 106/671 |
| 4,992,103 | A | 2/1991 | Smart | |
| 5,281,265 | A | * 1/1994 | Liu | 106/35 |
| 5,624,489 | A | 4/1997 | Fu et al. | |
| 5,961,712 | A | 10/1999 | Sun et al. | |

FOREIGN PATENT DOCUMENTS

| | | |
|---|---|---|
| WO | WO-03/082765 | 10/2003 |
| WO | WO-2005/039508 | 5/2005 |

* cited by examiner

*Primary Examiner*—Karl E Group
*Assistant Examiner*—Noah S Wiese
(74) *Attorney, Agent, or Firm*—B. Aaron Schulman; Stites & Harbison PLLC

(57) ABSTRACT

The present invention deals with the initial hydration reaction of highly alkaline chemically bonded ceramic systems such as Ca-aluminate and Ca-silicate, exhibiting a controlled pH development, reduced from very high levels to be in a pH range of 7-9 by the use of an internal buffer system added to the CBC type biomaterial used. The invention is especially intended for endodontic, orthopaedic applications and/or soft tissue applications and/or drug delivery carrier applications.

11 Claims, 1 Drawing Sheet pH with x-axis log (time) in hours –

Rapid pH change within minutes.

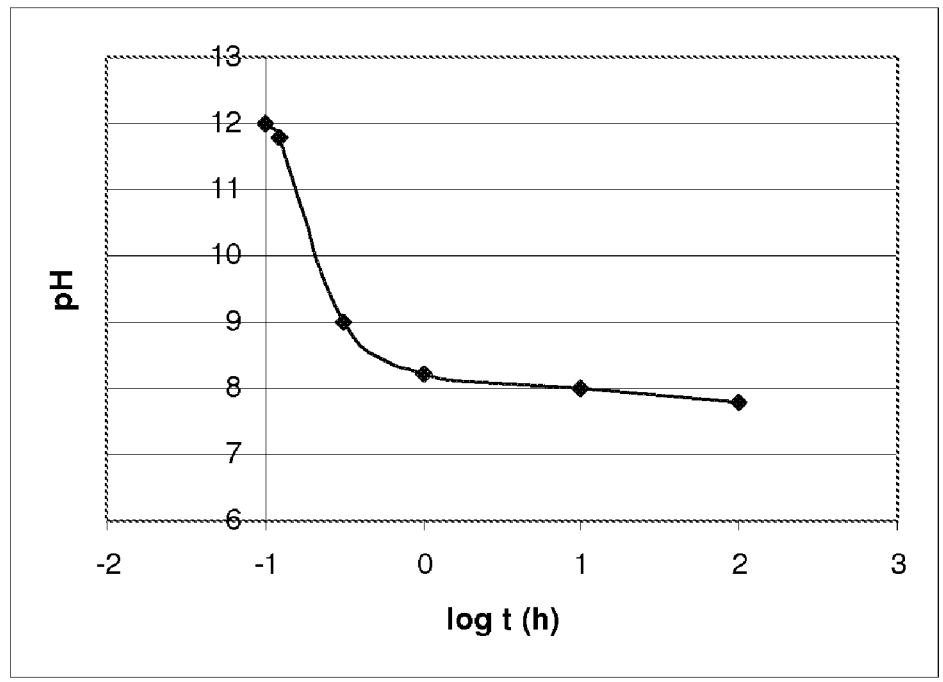
Figure 1. pH with x-axis log (time) in hours –
Rapid pH change within minutes.
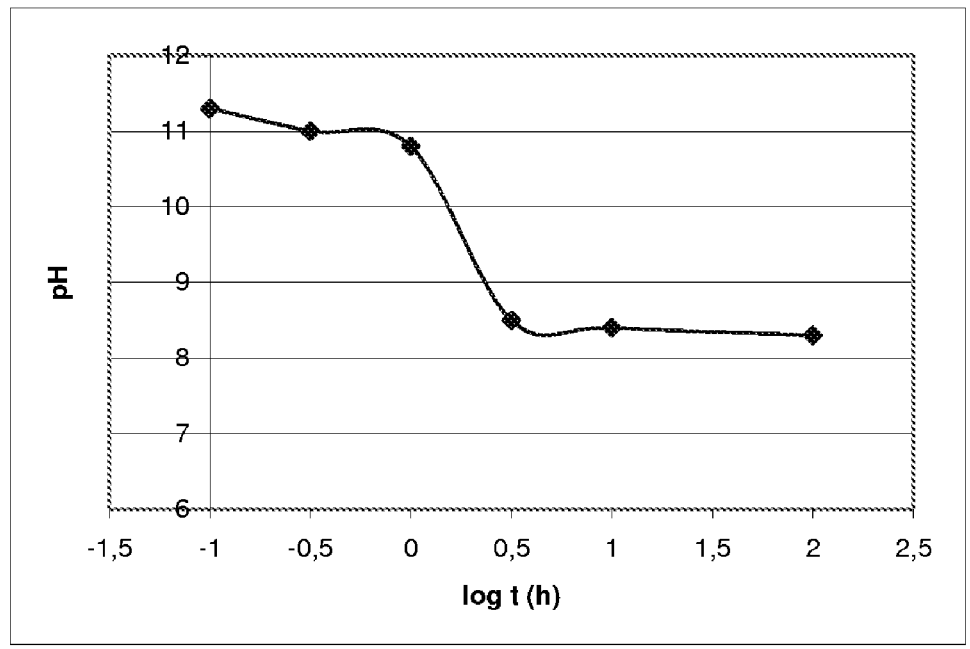
Figure 2. pH level with x-axis log (time) in hours
– high pH prolonged approx. 1 h

POWDERED CBC SYSTEM WITH IMPROVED REACTION FEATURE

CROSS-REFERENCE TO RELATED APPLICATIONS

This application claims the benefit of U.S. Provisional Application Ser. No. 60/748,176, filed Dec. 8, 2005, incorporated herein by reference.

TECHNICAL FIELD

For medical devices which are formed in vivo the biocompatibility profile, especially during the initial reactive stage, is of specific importance. Many chemically bonded ceramics, and especially aluminate and silicate ceramics, which are formed as a result of an acid-base reaction, exhibit a high pH-range during the first hours. The present invention is directed to such compositions exhibiting a lowered pH range during the initial reaction period. The composition of the invention is especially intended for endodontic and orthopaedic applications, and also for soft tissue applications.

STATE OF THE ART AND PROBLEM

Implants that are to interact with the human body should advantageously be composed of materials having a good biocompatibility and bioactivity. An example of such a material is the class known as "chemically bonded ceramics" (CBC). The hardening of such materials is accomplished by chemical reaction with water, involving formation of stable hydrates, precipitation and crystallization thereof, which reaction takes place already at ambient temperature, such as for example in in vivo conditions. Chemically bonded ceramics have been shown to be bioactive in the sense that the materials in contact with phosphate solution (both in vitro and in vivo) form apatite in the contact zone between the biomaterial and the tissue.

Examples of such materials are the high strength CBC materials, which are based on Ca-aluminates and/or Ca-silicates, such as those described in SE463493, SE502987, WO 2000/021489, WO 2001/076534, WO 2001/076535, WO 2004/037215, WO 2004/00239 and WO 2003/041662. Said materials have been proposed for use in dental applications.

It would be desirable to be able to use such materials also in endodontic and orthopaedic applications.

Accordingly, it is an object of the present invention to improve the characteristics of the above materials in order to make them better suited for use in endodontic and orthopaedic applications.

For a CBC material producing an initial pH of $\geq 10$ on hydration the problem has been solved by means of the characterizing features of claim 1, according to which a solid phase buffer component is included in the CBC material forming powder composition.

SUMMARY OF THE INVENTION

The present inventors have found the inherently high pH value produced on hydration of many of the above prior art materials to make them less suited for use in endodontic and orthopaedic applications. As an example, most of the above Ca-aluminates and Ca-silicates hydrate in the basic pH-range of 10.5-12.5. This is especially believed to be a problem when said materials are to be used in applications other than dental applications and coatings on implants requiring larger amounts of the material.

The high pH value has been found to be connected with the initial hydration reaction of the material (see Tables 1 and 2 for Ca-aluminate and Ca-silicate, respectively). After the initial reaction the subsequent diffusion controlled reaction is controlled with regard to pH by the body liquid buffer system. Accordingly, after the initial hydration reaction, which has been found to be intense during the first hours up to one day, and especially during the first 4 hours, the use of Ca-aluminate and Ca-silicate systems should no longer be problematic.

The present inventors have now found that the initially high pH value produced on hydration can be successfully controlled to be within a reduced pH range already after 1 hour of hydration reaction by including a solid phase buffer component in the powder system forming the CBC material. Such powder system is provided for in claim 1. The system is especially intended for endodontic and orthopaedic applications.

According to the present invention the period of time during which an alkaline CBC system produces a critically high pH value in vivo can be markedly reduced.

Therefore, the inventive CBC system containing the buffer component will to a lesser extent affect the endogenous buffer system than the prior art alkaline CBC system not having a buffer component, thus making the inventive system more tolerable in vivo.

The use of a buffer component in the solid state according to the invention allows for a very effective buffering action.

Also, the use of buffer components exhibiting anions which can form part of the structure of chemically bound material makes the buffering component a more integral part of the system and allows for larger amounts of the buffer component to be used.

In addition to endodontic and orthopaedic applications, the material of the invention is also believed to be suitable for soft tissue applications by virtue of the reduced pH during the initial hydration reaction.

Further features and advantages of the present invention will be evident from the following detailed description and dependent claims.

The system of the invention also allows for incorporation of pH sensitive drugs and/or bone growth promoting agents, prophylactically and/or diagnostically active agents to be released subsequently by the chemically bound ceramic biomaterial in vivo. Examples of such drugs include therapeutic agents for many areas, e.g. pain relief, anesthetics, anti-infective agents and anti-inflammatory drugs, drugs for treatment of immunological disorders, hormonal disruption, clotting behavior, cancer, and combinations thereof. In these cases the agents can be contained in the porous implant, precursor or implant material or as separate porous granules.

BRIEF DESCRIPTION OF THE ATTACHED DRAWINGS

FIG. 1 shows the pH change over time of a system according to the invention producing a rapid controlled pH change.

FIG. 2 shows a plot of the pH as a function of time for a controlled and delayed pH reduction after a given period of time to optimize the hydration during the first 30-60 minutes, and thereafter a substantially reduced pH to a more biocompatible range.

DETAILED DESCRIPTION OF THE INVENTION

The internal buffer system is composed of a buffering salt of mono-, di-, tri- and/or tetravalent acids. The salts are typically salts of mineral acids of the type [Me:H:Anion], wherein:

Me=Na, K, Mg, Ca or similar elements;
Anion=$CO_3^{2-}$, $PO_4^{3-}$, $SO_3^{2-}$, $SO_4^{2-}$, $SiO_4^{4-}$ or fluoride; and
H=one or more hydrogen ions.

In one embodiment the CBC material of the invention is combined with an added acid as dry component in inert particle porosities for a rapid change early in the hydration process, such as improved early-age mechanical properties, as described in WO 2005/039508.

The pH change over time is presented in FIG. 1. Another advantage of a controlled pH reduction after a given period of time according to the invention is the possibility to optimize the hydration during the first 30-60 minutes, and thereafter obtaining a substantially reduced pH to a more biocompatible range. See the pH vs. time plot in FIG. 2. In such embodiment, in order to achieve an optimized hydration during the first 30-60 minutes, the buffering salt can be impregnated in porous granules of the component forming the chemically bonded ceramic material and/or in an additional porous inert phase. The diffusion of the buffer salt into the surrounding media will thereby be delayed.

According to the present invention the initial hydration reaction of very alkaline systems, such as Ca-aluminate and Ca-silicate (with an initial pH value on hydration of 11-12.5), can be effectively controlled to be in a reduced pH range of 7.5-10 already after 1 hour of hydration reaction, preferably within the range 7.5 to 9.5, and more preferably within the range of 7.5 to 9.0, by the use of an internal buffer system added to the powdered biomaterial of CBC type used. The internal buffer system is composed of a buffering salt of mono-, di-, tri- and/or tetravalent mineral acids. The salts are typically acidic salts of the type [Me:H:Anion], wherein:

Me=Na, K, Mg, Ca and similar elements;
Anion=$CO_3^{2-}$, $PO_4^{3-}$, $SO_3^{2-}$, $SO_4^{2-}$, $SiO_4^{4-}$ and fluoride; and
H=one or more hydrogen ions.

Very attractive are the acid salts forming the ions $HF_2^-$, $HCO_3^-$, $HP_4^{2-}$ and $H_2PO_4^-$ in aqueous solutions.

Examples of most suitable salts for use as the buffer are: $KHF_2$, $NaHCO_3$, $Mg(Ca)HPO_4$, $Na_2HPO_4$ and $NaH_2PO_4$.

The pH development has been found to depend on three major material sources; the solid raw material (CBC), the general hydration liquid used, and the body liquid encountered after implantation. Especially effective with high buffering capacity are the solid buffers according to the present invention. The buffering capacity can be expressed as mM OH—. The capacity is as high as 100 mM, corresponding to a pH change from approximately 13 to near neutral, i.e. pH 7-8. The buffering capacity of body liquids are considerably lower due to two aspects; the ion buffering capacity expressed as mM is considerably lower, and secondly the body liquids are external and thus pH reduction is diffusion-time restricted, as generally described in Ceramics, Cells and Tissues, Ed Ravaglioli and Krajewski, pp 200-201, published by IS-TEC-CNR-Faenza, May 2005. The buffering salts are preferably added in solid form to the ceramic powder. However, the salts could also be dissolved in the hydrating liquid, in which case the required buffer salt could be added to the hydration liquid only, or to both liquid and powder in any desired ratio.

The skilled person having read the present disclosure can readily establish the necessary amount of a given buffer salt to be added to a given amount of the composition in order to achieve a desired pH value on hydration, e.g. merely by routine pH measurements. With reference to Table 3 it can be seen that the necessary amount is dependent upon the specific CBC material used. For example, the silicate material is more alkaline than the aluminate material and will consequently require a larger amount of any given buffer salt.

In general the amount of the buffer is selected so as to obtain a pH value within the range of 7.5 to 10 after 1 hour of hydration reaction, preferably within the range 7.5 to 9.5, and more preferably within the range of 7.5 to 9.0.

The amount of the buffer should not exceed 30% by volume of the total volume of the constituents of the powder system in the dry state, since otherwise the mechanical properties of the bound material will be negatively effected. On the other hand, an amount of less than 3% by volume of any buffer salt will not produce a sufficient pH controlling effect.

With reference to Tables 1 and 2 it can be seen that the pH in phosphate buffer solution (i.e. a simulated body fluid), declines more rapidly than in water. A volume of 3% of the acid buffer salt of the invention is generally sufficient to produce a pH reduction at 1 hour of hydration of at least 0.5.

With reference to the total hydrating system, i.e. the powdery constituents together with hydration liquid, a preferred amount the acidic buffer salt is within the range of 5-20% by weight, and more preferably 5-10% by weight.

Suitable Ca-aluminate and/or Ca-silicate systems for implants which can be used in the present invention are described in e.g. Swedish patent applications Nos.: SE 0200637-7, SE 0203223-3 and SE 0203324-1. Additives which can be used are described in SE 463493, SE 502987, WO 00/21489, WO 01/76534, WO 01/76535, WO 2004/037215 and WO 2003/041662, the relevant contents of which are incorporated herein by reference.

As disclosed in WO 2005/039508, in order to improve the controllability of the composition's initial viscosity and consistency, and early-age properties (initial strength, pore closure, translucency and early obtained bioactivity), a polycarboxylic acid or a copolymer or a salt or an ester thereof having a molecular weight of 100-250,000, preferably 1000-100,000 could be added to the powder. The amount of the acid or the copolymer, salt or ester thereof must however be selected so as not interfere with the buffering action of the salt, or compromise the desired mechanical properties of the hardened material. A suitable amount is believed to be within the range of 1-15% and preferably 2-5% by weight, based on the powdered material including any dry additives.

EXAMPLES

Ca-aluminate (CA) and Ca-silicate ($C_3S$) were synthesized at 1410 and 1380° C., respectively, in a conventional sintering furnace for 6 h. The materials were crushed and thereafter milled for 72 h in a rotating mill using ceramics containers and with the milling media of Silicon nitride balls (15 mm in diameter) and iso-propanol as liquid. After thin film evaporation the powder was pressed to small pellets. The pellet dimensions were: length, l=6 mm; and diameter, d=4 mm. The compact density was approximately 59%.

In tables 1 and 2 pH development for a pure Ca-aluminate and a pure Ca-silicate phase (0-30 days with exchange of liquid after each test time), respectively, are shown. In table 3 pH development for the systems in examples (tables 1 and 2) with different amounts of three different internal buffer systems added ($KHF_2$, $NaHCO_3$ and $MgHPO_4$ and $NaH_2PO_4$) according to table 3 below, are presented. The amount of added internal buffer was a=5, b=10 and c=20 wt-% of the weight of the hydrating system used.

TABLE 1

The pure system Ca-aluminate and pH development in
water (W) and phosphate buffer solution (PBS).

| Medium | Time zero | 1 h | 4 h | 24 h | 1 week | 1 month |
|---|---|---|---|---|---|---|
| W | 11.5 | 11.3 | 11.0 | 9.4 | 8.8 | 8.4 |
| PBS | 11.5 | 10.2 | 9.5 | 8.0 | 7.8 | 7.8 |

TABLE 2

The pure system Ca-silicate and pH development in
water (W) and phosphate buffer solution (PBS).

| Medium | Time zero | 1 h | 4 h | 24 h | 1 week | 1 month |
|---|---|---|---|---|---|---|
| W | 12.4 | 12.0 | 11.8 | 10.5 | 9.0 | 9.0 |
| PBS | 12.4 | 11.5 | 10.5 | 9.5 | 9.0 | 9.0 |

TABLE 3

Ca-aluminate (CA) and two different types of internal buffer components in
phosphate buffer solution, (1-3 = $KHF_2$, 4-6 = , $NaHCO_3$) and Ca-silicate ($C_3S$) and
two different types of internal buffer components in water (7-9 = and $MgHPO_4$ and
10-12 = and $NaH_2PO_4$).

| | Type | | | | | | | | | | | |
|---|---|---|---|---|---|---|---|---|---|---|---|---|
| | 1 a = 5 | 2 b = 10 | 3 b = 20 | 4 a = 5 | 5 b = 10 | 6 c = 20 | 7 a = 5 | 8 b = 10 | 9 c = 20 | 10 a = 5 | 11 b = 10 | 12 c = 20 |
| After 5 min[1] | 11.5 | 11.5 | 10.5 | 11.5 | 11.0 | 10.0 | 12.3 | 11.8 | 11.5 | 12.0 | 11.2 | 10.2 |
| 5 min[2] | 11.3 | 11.3 | 10.0 | 11.0 | 10.5 | 9.5 | 12.0 | 11.5 | 11.2 | 11.5 | 10.5 | 9.8 |
| 1 h | 9.5 | 9.3 | 9.0 | 9.5 | 9.0 | 9.0 | 10.0 | 10.0 | 9.8 | 9.0 | 8.5 | 8.0 |
| 4 h | 9.0 | 9.0 | 8.5 | 8.5 | 8.0 | 8.0 | 10.0 | 10.0 | 9.7 | 8.5 | 8.0 | 8.0 |
| 24 h | 8.0 | 8.0 | 7.8 | 8.5 | 8.0 | 8.0 | 9.5 | 9.0 | 9.0 | 8.0 | 8.0 | 8.0 |
| 1 w | 8.0 | 8.0 | 7.8 | 8.5 | 8.0 | 8.0 | 8.5 | 8.0 | 8.0 | 8.0 | 8.0 | 7.7 |
| 1 m | 8.0 | 8.0 | 7.8 | 8.0 | 8.0 | 7.5 | 8.0 | 8.0 | 8.0 | 8.0 | 8.0 | 7.7 |

[1] After 5 min means 5 min after start of mixing the powder and liquid.
[2] 5 min means 5 min after mixing is completed. The mixing takes approx. 2 minutes.

The invention claimed is:

1. A powdered composition forming a chemically bonded ceramic biomaterial on hydration thereof, comprising (a) an alkaline component comprised of a material selected from the group consisting of calcium-aluminates, calcium-silicates and combinations thereof and forming a chemically bonded ceramic material, an initial pH of $\geq 10$, on hydration thereof, and further comprising (b) a solid buffering salt of a mono-, di-, tri- or tetravalent mineral acid in an amount of 3-30% by volume further comprising an ingredient selected from the group consisting of pH sensitive drugs and/or bone growth promoting agents, prophylactically and/or diagnostically active agents to be released subsequently by the chemically bound ceramic biomaterial in vivo, therapeutic agents for pain relief, anesthetics, anti-infective agents and anti-inflammatory drugs, drugs for treatment of immunological disorders, hormonal disruption, clotting behavior, cancer, and combinations thereof.

2. The powdered composition of claim 1, wherein the buffering salt is of the type [Me:H:Anion], wherein:
Me=Na, K, Mg or Ca;
Anion=$CO_3^{2-}$, $PO_4^{3-}$, $SO_3^{2-}$, $SO_4^{2-}$, $SiO_4^{4-}$ or fluoride; and
H=one or more hydrogen ions.

3. The powdered composition of claim 1, wherein the composition undergoes a solid buffer phase, and wherein the solid buffer phase produces the ions selected from $HF_2^-$, $HCO_3^-$, $HPO_4^{2-}$ and $H_2PO_4^-$.

4. The powdered composition of claim 1 wherein component (a) exhibits an initial pH value of $\geq 11$ on hydration thereof.

5. The powdered composition of claim 1 wherein the amount of (b) is selected such that a pH of 7.5-10 is obtained after 1 hour of hydration of composition.

6. The powdered composition of claim 1 wherein the amount of (b) is selected such that a pH of 7.5-9.5 is obtained after 1 hour of hydration of composition.

7. The powdered composition of claim 1 wherein the amount of (b) is selected such that a pH of 7.5-9 is obtained after 1 hour of hydration of composition.

8. A powdered composition forming a chemically bonded ceramic biomaterial on hydration thereof, comprising (a) an alkaline component comprised of a material selected from the group consisting of calcium-aluminates, calcium-silicates and combinations thereof and forming a chemically bonded ceramic material, an initial pH of $\geq 10$, on hydration thereof, and further comprising (b) a solid buffering salt of a mono-, di-, tri- or tetravalent mineral acid in an amount of 3-30% by volume wherein the buffering salt (b) is impregnated in porous granules of component (a) and/or in an additional porous inert phase.

9. The powdered composition of claim 1 further comprising a conventional additive for controlling viscosity and setting of the composition.

10. A composition forming a chemically bonded ceramic biomaterial on hydration thereof, comprising (a) an alkaline component forming a chemically bonded ceramic material, an initial pH of $\geq 10$ on hydration thereof comprised of a material selected from the group consisting of calcium-aluminates, calcium-silicates and combinations thereof and (c) hydration liquid, and further comprising (b) a buffering salt of a mono-, di-, tri- or tetravalent mineral acid in an amount of 3-30% by volume based on the total volume of the constituents in dry state, or 5-20% by weight of the hydrating system, said composition further comprising an ingredient selected from the group consisting of pH sensitive drugs and/or bone growth promoting agents, prophylactically and/or diagnostically active agents to be released subsequently by the chemically bound ceramic biomaterial in vivo, therapeutic agents for pain relief, anesthetics, anti-infective agents and anti-inflammatory drugs, drugs for treatment of immunological disorders, hormonal disruption, clotting behavior, cancer, and combinations thereof.

11. A method of preparing the composition of claim 10, comprising the step of mixing (a) an alkaline component comprised of a material selected from the group consisting of calcium-aluminates, calcium-silicates and combinations thereof and forming a chemically bonded ceramic on hydration thereof and (c) hydration liquid, wherein a buffering salt of a mono-, di-, tri- or tetravalent mineral acid in an amount of 3-30% by volume based on the total volume of the constituents in dry state, or 5-20% by weight of the hydrating system is dissolved in the hydration liquid (c) and/or added to compound (a) said method further comprising adding an ingredient selected from the group consisting of pH sensitive drugs and/or bone growth promoting agents, prophylactically and/or diagnostically active agents to be released subsequently by the chemically bound ceramic biomaterial in vivo, therapeutic agents for pain relief, anesthetics, anti-infective agents and anti-inflammatory drugs, drugs for treatment of immunological disorders, hormonal disruption, clotting behavior, cancer, and combinations thereof.

\* \* \* \* \*